United States Patent [19]
Abidin et al.

[11] Patent Number: 5,528,811
[45] Date of Patent: * Jun. 25, 1996

[54] ARTICLE AND METHOD FOR SAFELY MOUNTING A BLADE ON A SURGICAL SCALPEL

[75] Inventors: Michael R. Abidin, Charlottesville, Va.; Steven P. Lehmbeck, Baltimore, Md.

[73] Assignee: Bloom & Kreten, Towson, Md.; a part interest

[*] Notice: The portion of the term of this patent subsequent to May 18, 2014, has been disclaimed.

[21] Appl. No.: 435,668

[22] Filed: May 5, 1995

Related U.S. Application Data

[62] Division of Ser. No. 245,009, May 18, 1994, Pat. No. 5,433,321.

[51] Int. Cl.$^6$ .......................... B23P 19/04; B65D 85/00; B26B 9/00
[52] U.S. Cl. ............................. 29/428; 30/339; 206/352; 206/354
[58] Field of Search ................... 30/339, 346.61; 29/235, 270, 428, 446; 53/492; 206/352, 356, 359, 370, 354

[56] References Cited

U.S. PATENT DOCUMENTS

| | | |
|---|---|---|
| 1,167,464 | 1/1916 | Young . |
| 1,448,305 | 3/1923 | Langbein ..................... 30/339 |
| 1,608,274 | 11/1926 | Grayson . |
| 2,131,358 | 9/1938 | Rothschild ..................... 30/125 |
| 2,866,542 | 12/1958 | Svirchev . |
| 3,447,181 | 6/1969 | Coker et al. ................... 15/104.94 |
| 3,543,918 | 12/1970 | Waterman ................................. 206/16 |
| 4,106,620 | 8/1978 | Brimmer et al. ..................... 206/363 |
| 4,120,397 | 10/1978 | Neumann ............................. 206/370 |
| 4,157,758 | 6/1979 | Kozlowski, Jr. ..................... 206/363 |
| 4,180,162 | 12/1979 | Magney ............................... 206/363 |
| 4,270,416 | 6/1981 | Thompson ............................. 81/3 R |
| 4,344,532 | 8/1982 | Eldridge, Jr. et al. ................. 206/370 |
| 4,395,807 | 8/1983 | Eldridge, Jr. et al. ................... 29/239 |
| 4,523,679 | 6/1985 | Paikoff et al. ....................... 206/370 |
| 4,730,376 | 3/1988 | Yamada ............................... 29/239 |
| 4,736,842 | 4/1988 | Uetake et al. ......................... 206/363 |
| 4,746,016 | 5/1988 | Pollak et al. ......................... 206/356 |
| 4,903,390 | 2/1990 | Vidal et al. .......................... 29/239 |
| 4,998,334 | 3/1991 | Pemberton et al. .................... 206/359 |
| 5,088,173 | 2/1992 | Kromer et al. ........................ 206/359 |
| 5,301,807 | 4/1994 | Donahue ............................... 206/370 |
| 5,361,902 | 11/1994 | Abidin et al. ......................... 206/370 |
| 5,363,958 | 11/1994 | Horan ................................. 206/356 |

OTHER PUBLICATIONS

Photocopies (front and back) of product packaging for "X–ACTO" No. 11 Fine Point blade Safety Dispenser.

Primary Examiner—Jimmy G. Foster
Attorney, Agent, or Firm—Leonard Bloom

[57] ABSTRACT

A blade package assembly assures that a blade may be mounted on a surgical scalpel easily, conveniently and safely during a surgical procedure in an operating room. The assembly includes a base and a pivoted cover. The base supports a blade, and the cover at least partially encloses the blade. A pin on the base is received in a hole in the blade, and a ledge on the base supports the rear end portion of the blade. The scalpel has a forwardly-extending cleat received in a slot on the blade, and the scalpel with the blade mounted thereon may be lifted up and away to clear the package.

3 Claims, 3 Drawing Sheets

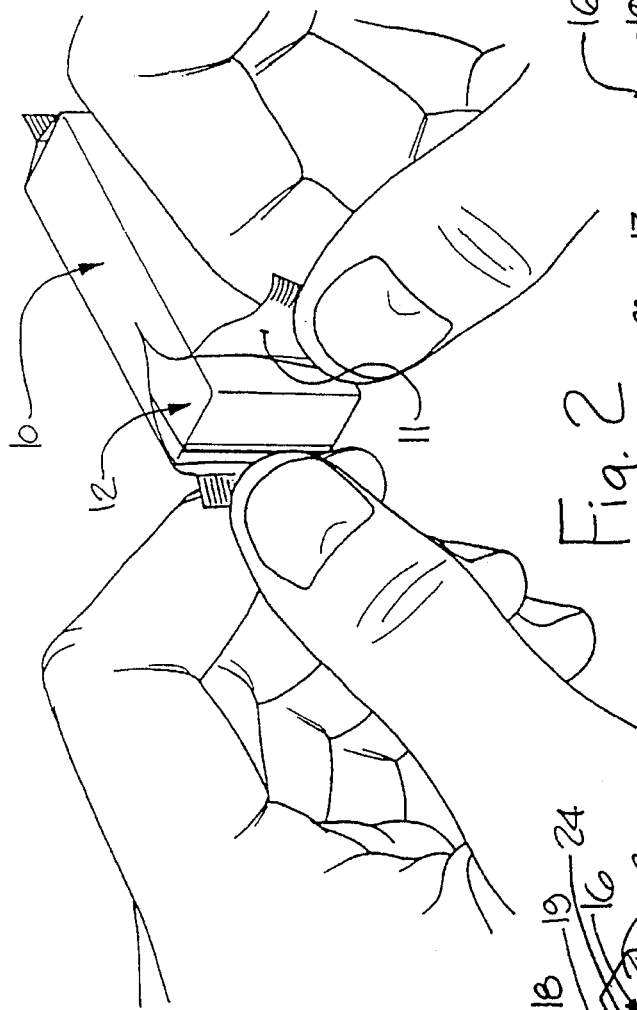
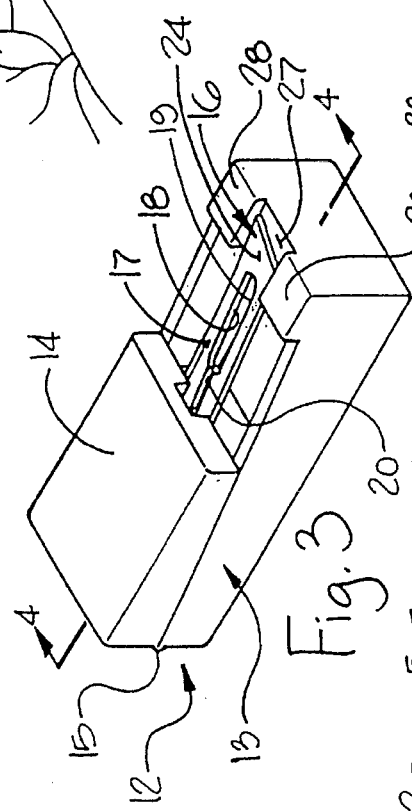
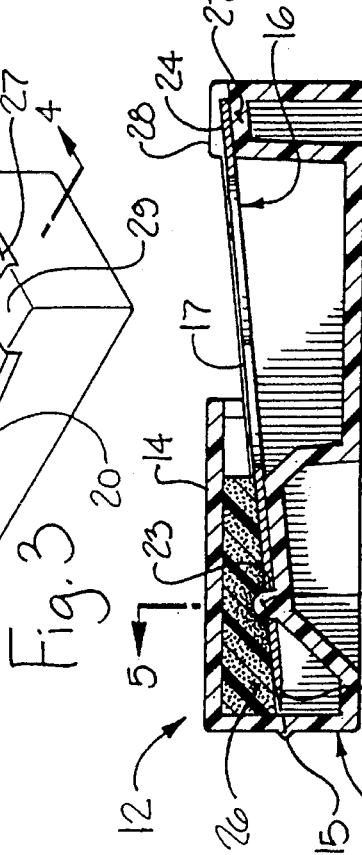
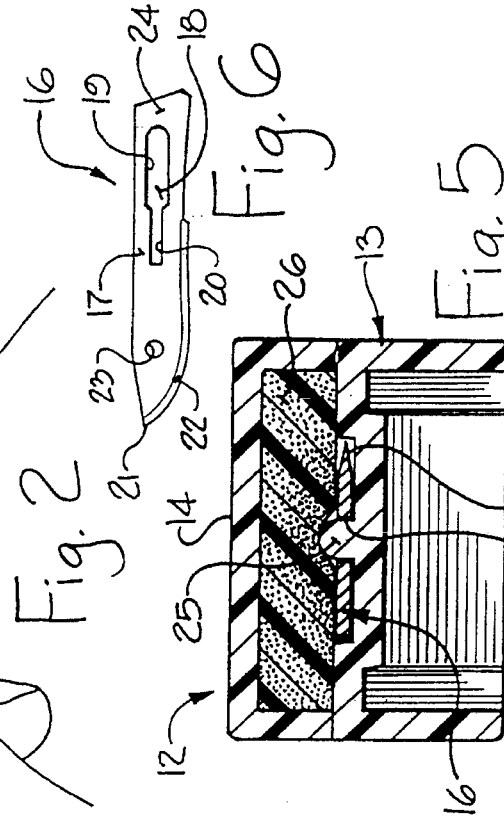

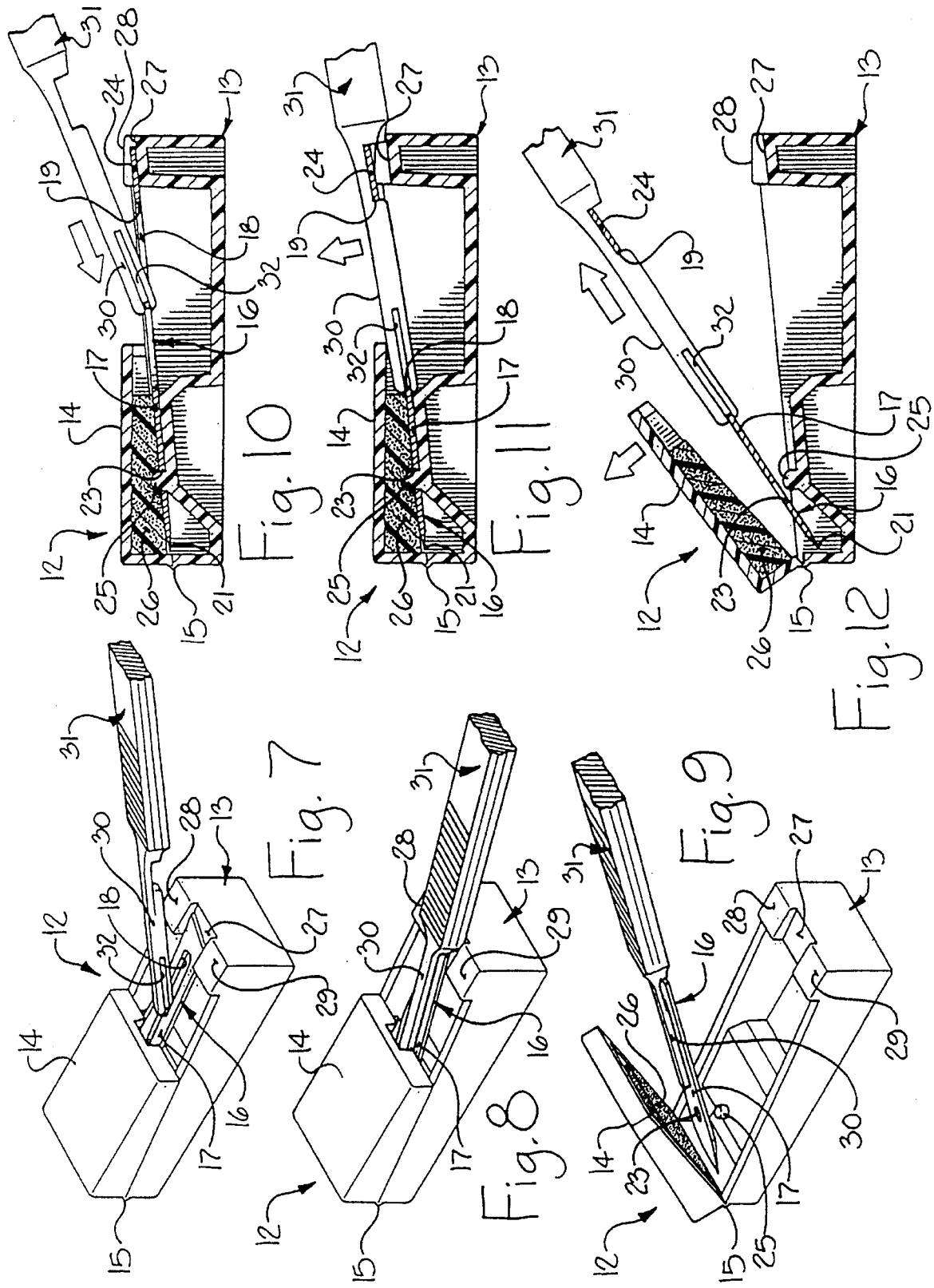

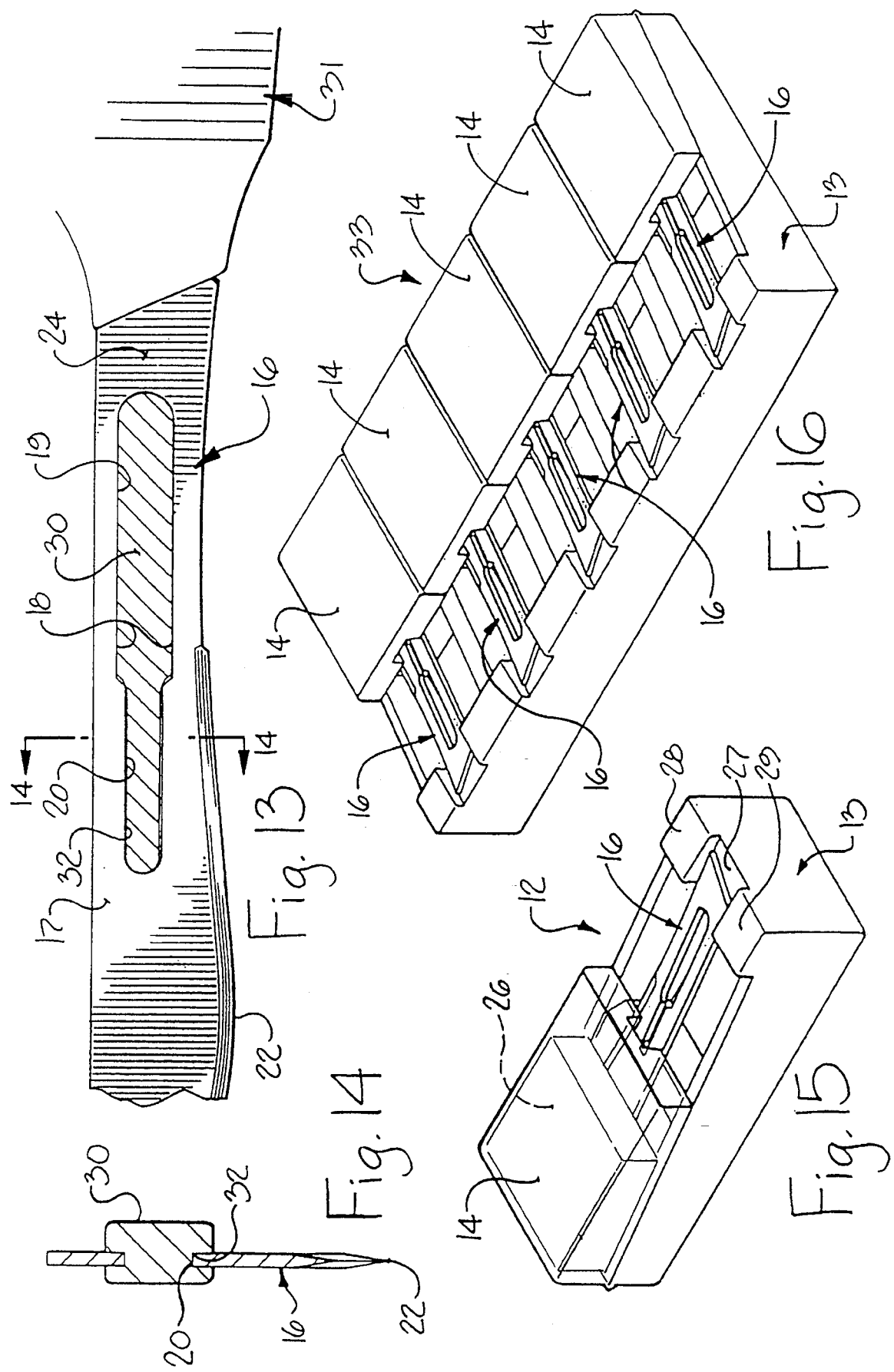

ARTICLE AND METHOD FOR SAFELY MOUNTING A BLADE ON A SURGICAL SCALPEL

This application is a division of application Ser. No. 08/245,009, filed May 18, 1994, U.S. Pat. No. 5,433,321.

FIELD OF THE INVENTION

The present invention relates to a package for a surgical scalpel blade and, more particularly, to a blade package for safely mounting the blade on a forwardly-extending cleat on the scalpel.

BACKGROUND OF THE INVENTION

Surgical scalpel blades are usually packaged individually in an aluminum foil wrap and are irradiated for sterilization purposes. The sterile foil wrap is torn open in the operating room ("O.R.") in a hospital or clinic, and the blade is removed and mounted on a surgical scalpel. The scalpel has a forwardly-projecting portion (referred to in the art as a "cleat") and this cleat is inserted within a longitudinal closed slot formed in the blade, thereby mounting the blade on the scalpel. The blade is relatively thin and flexible, the cleat on the scalpel has a groove to receive the blade, and the mounting is with a slight "snap" fit or "click".

Some scalpel blades, which are used in microsurgery, are super sharp and are packaged in a molded plastic package consisting of a base and a pivoted cover.

The scalpel blades are usually changed several times during a medical procedure in the O.R., since it is imperative that the sharpness of the blades be maintained. The blades are usually changed by a nurse or O.R. technician (called the "tech").

Whether the blade is packaged in an aluminum foil or in a molded plastic package, the blade is removed therefrom; and during the blade mounting process, the tech holds the scalpel in one hand and the blade in the other hand and slips the blade on to the cleat on the scalpel. These blades are roughly an inch to an inch-and-a-half long and (of course) are razor sharp, so it is not at all uncommon for the tech to be nicked or cut while mounting one of the blades, thereby causing blood flow.

If the patient is H.I.V.-infected, the tech may sero-convert and become H.I.V.-infected leading to the deadly AIDS disease. Conversely, if the tech is an H.I.V. carrier, the patient or the other health care providers in the O.R. are at risk. The same is true with respect to hepatitis or other infectious diseases.

The nurse or tech is very often under intense pressure in the O.R. and may become temporarily distracted while in the process of changing blades. This tends to aggravate the existing problem.

SUMMARY OF THE INVENTION

Accordingly, it is an object of the present invention to provide a safety blade package for a surgical scalpel, thereby avoiding cuts or nicks when installing a new blade on the scalpel.

It is another object of the present invention to provide a safety blade package that may be manufactured conveniently and at relatively low cost, thereby facilitating widespread marketing and distribution.

It is yet another object of the present invention to provide a safety blade package that is "user friendly" so that the hospital nurses and O.R. techs will immediately understand the use thereof and will readily appreciate its ease, convenience and safety features.

In accordance with the teachings of the present invention, a blade package for safely mounting a blade on a surgical scalpel is herein disclosed and claimed, wherein the blade includes a cutting edge and further includes a body portion having a slot formed therein, the body portion having a rear end portion, and wherein the scalpel has a forwardly-projecting cleat received within the slot in the blade. The blade package includes a base having a ledge supporting the rear end portion of the blade. The blade further has a hole formed therein; and the base further has an upstanding pin received in the hole in the blade, thereby mounting the blade on the base and preventing substantial movement of the blade within the package, and thereby preventing any inadvertent dulling of the cutting edge on the blade. As a result, the cleat on the scalpel may be inserted within the slot on the blade; and the scalpel with the blade mounted thereon may be lifted up and away from the base, thereby clearing the hole in the blade from the pin on the base.

Preferably, a cover is pivotably mounted on the base. The cover has a pivot axis which is substantially perpendicular to the pin and spaced therefrom; and the cover extends partially over the base, substantially covering the cutting edge of the blade, and exposing the slot formed within the blade, such that the cover is pivoted away from the base as the scalpel with the blade thereon is lifted away from the base.

In a preferred embodiment, the cover is transparent, such that the cutting edge on the blade is visible through the cover; and the cover carries a cushion bearing against the blade.

The ledge on the base supporting the rear end portion of the blade is canted downwardly in a direction towards the pin, such that the blade is inclined with respect to the base, thereby facilitating the insertion of the cleat on the scalpel into the slot on the blade. Preferably, the base is provided with a pair of spaced-apart raised lands, one on each side of the ledge on the base.

The present invention also provides an improved surgical blade comprising a main body portion having an elongated slot formed therein, a tip and a cutting edge, the elongated slot having a narrowed forward portion, and a hole formed in the blade between the tip and the narrowed forward portion of the elongated slot.

Viewed in another aspect, the present invention provides an improved method of mounting a blade on a surgical scalpel, wherein the scalpel has a forwardly-extending cleat. A sterile blade package is opened to obtain a blade package assembly; and this blade package assembly includes a base having a blade mounted thereon. The blade has a main body portion provided with a longitudinal slot, and the blade further has a tip and a cutting edge. The base is provided with a pivoted cover covering at least the tip of the blade. The cleat on the scalpel is inserted into the longitudinal slot in the blade, so that the blade is "snapped" on to the cleat; and the scalpel with the blade mounted thereon is moved up and away from the base to lift the cover and pivot it away from the base, thereby clearing the scalpel with the blade thereon from the blade package assembly.

These and other objects of the present invention will become apparent from a reading of the following specification taken in conjunction with the enclosed drawings.

BRIEF DESCRIPTION OF THE DRAWINGS

FIG. 1 is a pictorial view of a sterile blade package protected by a removable foil.

FIG. 2 is a further pictorial view, corresponding to FIG. 1, but showing the foil being removed for access to the blade package assembly of the present invention.

FIG. 3 is a perspective view of the blade package assembly including a base, a blade mounted on the base, and a partial cover pivotably mounted on the base for protecting the blade.

FIG. 4 is a cross-sectional view thereof, taken along the lines 4—4 of FIG. 3 and drawn to an enlarged scale, and showing an upstanding pin on the base, the pin being received within a hole in the blade, and further showing the rear end portion of the blade supported upon a ledge on the base, the blade preferably being inclined downwardly towards the pin.

FIG. 5 is a cross-sectional view thereof, taken along the lines 5—5 of FIG. 4 and showing how the cutting edge of the blade is maintained in a spaced relationship at all times with the blade package assembly, thereby precluding the blade from being dulled inadvertently.

FIG. 6 is a plan outline of the improved blade of the present invention.

FIG. 7 is a pictorial view showing the cleat on the scalpel initially being inserted into the slot on the blade.

FIG. 8 is a further pictorial view, corresponding substantially to FIG. 7, but showing the cleat on the scalpel fully seated within the slot on the blade.

FIG. 9 is a still further pictorial view, corresponding substantially to FIG. 8, but showing the scalpel (with the blade mounted thereon) being lifted up and away from the base, thereby pivoting the cover, and thereby clearing the hole in the blade from the pin on the base.

FIGS. 10–12 are schematic sequence views, corresponding to FIGS. 7–9, respectively, and showing how the blade may be safely and easily mounted on the scalpel in a matter of seconds.

FIG. 13 is a cross-sectional view, taken along the lines 13—13 of FIG. 12 and drawn to an enlarged scale, and showing the detailed construction of the slot in the blade and the cleat on the scalpel.

FIG. 14 is a cross-sectional view thereof, taken along the lines 14—14 of FIG. 13.

FIG. 15 is a pictorial view of a portion of FIG. 3, showing the cover as preferably transparent.

FIG. 16 is a further pictorial view, showing how a plurality of blades may be packaged in a single blade package, the package facilitating individual blade selection and mounting.

BRIEF DESCRIPTION OF THE PREFERRED EMBODIMENT

With reference to FIGS. 1–3, a sterile blade package 10 (FIG. 1) is wrapped in an aluminum foil 11 which is torn open (FIG. 2) in the O.R. (or other medical or hospital environment) to obtain the blade package assembly 12 of the present invention (FIG. 3).

With further reference to FIGS. 4 and 5, the blade package assembly 12 preferably comprises a single molded article and includes a base 13 and a cover 14 pivoted thereto by means of an integral reduced cross-section "living" hinge 15. The cover 14 extends partially over the base 13 and, preferably, the cover 14 is transparent (FIG. 15) along with the blade package assembly 12.

A blade 16 is mounted on the base 13. As shown more clearly in FIG. 6, the blade 16 has a main body portion 17 provided with a longitudinal slot 18. This slot 18 includes a rearward portion 19 and a narrowed forward portion 20. The blade 16 further has a tip 21, a bottom cutting edge 22, a hole 23 between the tip 21 and the slot 20, and a rear end portion 24 beyond the slot 20.

The base 13 has an upstanding pin 25 which is substantially perpendicular to the pivot axis of the cover 14 and spaced therefrom. This pin 25 is received in the hole 23 in the blade 16, thereby positioning the blade 16 on the base 13. The cover 14, in turn, is provided with a cushioned pad 26 of foam plastic (or other suitable material) to trap the blade 16 between the base 13 and the cover 14.

The base 13 further has a ledge 27 supporting the rear end portion 24 of the blade 16. Preferably, the ledge 27 is elevated so that the blade 16 is canted downwardly, as shown more clearly in FIG. 4. The base 13 further has a pair of spaced-apart raised lands 28 and 29, respectively, one on each side of the ledge 27.

This arrangement prevents undesired movement of the blade 16 (which would otherwise inadvertently dull the cutting edge 22 of the blade 16).

The operation of the invention and its inherent features and advantages are illustrated in FIGS. 7–12, respectively.

The blade 16 is mounted on the forwardly-extending cleat 30 of a surgical scalpel 31. Preferably (but not necessarily) the scalpel 31 is a guarded surgical scalpel as disclosed and claimed in U.S. Pat. No. 5,250,063 issued Oct. 5, 1993 and U.S. Pat. No. 5,275,606 issued Jan. 4, 1994 to the present inventors (applicants). It will be appreciated by those skilled in the art, however, that the present invention is equally applicable to conventional non-guarded scalpels, if desired.

As shown more clearly in FIGS. 7 and 10, the cleat 30 on the scalpel 31 is initially inserted into the rearward portion 19 of the slot 18 in the blade 16. The cleat 30 is then advanced forwardly such that the cleat 30 is fully seated within the slot 18 (which may be with a slight "click" or "snap" fit) as shown more clearly in FIGS. 8 and 11. Thereafter, the scalpel 31 with the blade 16 mounted thereon is lifted up and away from the base 13 (FIGS. 9 and 12) to pivot the cover 14 away from the base 13 and, more significantly, to clear the hole 23 in the blade 16 from the pin 25 on the base 13.

The entire operation of thus mounting the blade 16 on the scalpel 31 is easy and convenient, takes only a few seconds, and assures that the user will not be cut or nicked accidentally.

With reference to FIGS. 13 and 14, the cleat 30 on the scalpel 31 has a groove 32 formed therein to receive the slot 18 on the blade 16. These blades 16 are in widespread use in hospitals and clinics. However, it will be appreciated by those skilled in the art that the present invention is not necessarily confined thereto but, rather, is equally applicable to other surgical blade designs and configurations.

With reference to FIG. 16, the teachings of the present invention are equally applicable to a multi-blade package 33 having a plurality of blades 16 in a side-by-side relationship therein. This multi-blade package 33 would be contained in a single sterile package (not shown) which would be opened in the O.R.

The surgical scalpel blades 16 are razor sharp and can become dulled very quickly during a surgical procedure. It is important for the surgeon to have a very sharp "fresh" blade readily available. During a typical operation, the blades 16 may be changed around a half dozen times. This invention assures that the blades 16 may be quickly, easily and safely mounted on the scalpel 31 during the surgical procedure.

Moreover, it is significant that the blade does not move during the mounting process (unlike the prior art razor blade dispensers and injectors) and that the mounting of the blade involves basically two steps: first, insertion of the scalpel and, second, lifting of the scalpel (with the blade thereon) to pivot the cover and clear the blade package assembly. This movement is foolproof, convenient, safe, takes only a few seconds, and is readily understood by the O.R. techs, assistants and surgeons.

As disclosed herein, the mounting of the blade on the scalpel is basically a two-hand operation: one hand holding the blade package assembly 12, and the other hand holding the scalpel 31. However, if desired, a ledge or suitable mounting may be provided on the tray table (not shown) for retaining the blade package assembly 12, so that only the scalpel 31 is held. This is a one-hand operation.

Obviously, many modifications may be made without departing from the basic spirit of the present invention. Accordingly, it will be appreciated by those skilled in the art that within the scope of the appended claims, the invention may be practiced other than has been specifically described herein.

We claim:

1. The method of mounting a blade on a surgical scalpel, comprising the steps of providing a scalpel having a forwardly-extending cleat, providing a sterile blade package, opening the sterile blade package to obtain a blade package assembly, the blade package assembly including a base having a blade mounted thereon, the blade having a main body portion provided with a longitudinal slot, and the blade further having a tip and a cutting edge, providing a piloted cover on the base, the pivoted cover covering at least the tip of the blade, inserting the cleat on the scalpel into the longitudinal slot in the blade, so that the blade is "snapped" on to the cleat, and moving the scalpel with the blade mounted thereon up and away from the base to lift the cover and pivot it away from the base, thereby clearing the scalpel with the blade thereon from the blade package assembly.

2. The method of claim 1, further including the steps of providing an upstanding pin on the base, and providing a hole in the blade receiving the pin, thereby assuring that the cutting edge on the blade will not become dulled inadvertently due to movement of the blade within the package, and clearing the blade from the pin when the scalpel with the blade thereon is lifted up and away from the base.

3. The method of mounting a blade on a surgical scalpel, comprising the steps of providing a scalpel having a forwardly extending cleat, providing a sterile blade package, opening the sterile blade package, the blade package including a base having a blade mounted thereon, the blade having a main body portion provided with a longitudinal slot, and the blade further having a tip, a rear end portion and a cutting edge, the base having a ledge supporting the rear end portion of the blade, inserting the cleat on the scalpel into the longitudinal slot in the blade, so that the blade is "snapped" on to the cleat, and moving the scalpel with the blade mounted thereon up and away from the base, thereby clearing the scalpel with the blade thereon from the blade package, further including the steps of providing an upstanding pin on the base, and providing a hole in the blade receiving the pin, thereby preventing substantial movement of the blade within the blade package, assuring that the cutting edge on the blade will not become dulled inadvertently due to movement of the blade within the blade package, and clearing the blade from the pin when the scalpel with the blade thereon is lifted up and away from the base.

* * * * *